United States Patent

Ashman et al.

[11] Patent Number: 5,209,752
[45] Date of Patent: May 11, 1993

[54] LATERAL OFFSET CONNECTOR FOR SPINAL IMPLANT SYSTEM

[75] Inventors: Richard B. Ashman, Dallas, Tex.; Michael C. Sherman, Memphis, Tenn.

[73] Assignee: Danek Medical, Inc., Memphis, Tenn.

[21] Appl. No.: 803,325

[22] Filed: Dec. 4, 1991

[51] Int. Cl.⁵ ............................................. A61B 17/56
[52] U.S. Cl. ..................................... 606/61; 606/72
[58] Field of Search ................. 606/60, 61, 71, 14 74, 606/53

[56] References Cited

U.S. PATENT DOCUMENTS

| | | | |
|---|---|---|---|
| 4,448,191 | 5/1984 | Rodnyansky | 606/61 |
| 4,653,481 | 3/1987 | Howland et al. | 128/69 |
| 4,655,199 | 4/1987 | Steffee | 128/69 |
| 4,719,905 | 1/1988 | Steffee | 128/69 |
| 4,771,767 | 9/1988 | Steffee | 128/69 |
| 5,002,542 | 3/1991 | Frigg | 606/61 |
| 5,084,049 | 1/1992 | Asha et al. | 606/61 |
| 5,102,412 | 4/1992 | Rogozinski | 606/61 |

OTHER PUBLICATIONS

TSRH Lumbar System, by Danek Medical, Inc.
TSRH Spinal Implant System, Surgical Technique Manual, copyright 1990 by Danek Medical, Inc.

Primary Examiner—Robert A. Hafer
Assistant Examiner—Brian E. Hanlon
Attorney, Agent, or Firm—Woodard, Emhardt, Naughton, Moriarty & McNett

[57] ABSTRACT

A lateral offset connector is provided for engaging a spinal rod to a vertebral fixation element, such as a hook or a bone screw. The lateral offset connector includes a head portion from which a pair of parallel arms extend to form a slot opening between the arms. The arms are configured with grooves on their underside for receiving the spinal rod. The slot opening between the arms is configured to receive an eyebolt engagement assembly therebetween. The eyebolt is disposed between the arms of the connector and a nut is threaded onto the threaded post of the eyebolt to clamp the spinal rod between the eyebolt and the offset connector arms. The offset connector further includes a threaded post extending from the end of the connector for engagement with the spinal fixation component, such as the bone screw or hook. A nut clamps the fixation component between a rounded shoulder of the connector and the nut. The plurality of grooves in the arms of the connector provides means for readily engaging a plurality of vertebral fixation elements to a spinal rod where the the fixation elements are not colinear along the vertebral column, that is where the lateral distances of the fixation elements relative to the spinal rod varies along the length of the rod. The lateral offset connector of this invention, therefore, eliminates the need for contouring the rod in the saggital plane.

4 Claims, 1 Drawing Sheet

LATERAL OFFSET CONNECTOR FOR SPINAL IMPLANT SYSTEM

BACKGROUND OF THE INVENTION

The present invention broadly concerns devices for use in spinal implant systems, particularly those using spinal rods contoured for connection at various locations along the length of the spinal column. More specifically, the invention concerns a device for fixing the spinal rod to a fixation element of the implant system which provides direct engagement to a vertebra of the spinal column.

Several techniques and systems have been developed for use in correcting and stabilizing spinal curves and facilitating spinal fusion. In one system, a bendable rod is longitudinally disposed adjacent the vertebral column and is fixed to various vertebrae along the length of the column by way of a number of fixation elements. A variety of fixation elements can be provided, such as hooks or bone screws, which are configured to engage specific portions of the vertebra.

An example of one such system is the TSRH ® spinal system of Danek Medical, Inc. In this system, the hooks or screws are engaged to the spinal rod by way of eyebolts. As is well known in the art, the eyebolts are threaded onto the spinal rod and captured within yokes on the fixation hook or screw. A nut is threaded onto a threaded post of the eyebolt to clamp the yoke and rigidly fix the hook or screw element to the spinal fixation rod. Details of the TSRH spinal implant system are disclosed in the "Surgical Technique Manual" provided by Danek Medical, Inc., published in 1990, which disclosure is incorporated herein by reference.

It is the goal of the surgeon using such spinal implant systems to apply the vertebral fixation elements (hooks and/or screws) to the spine in the appropriate anatomic position, and then to engage each fixation element to the spinal rod. Once the spinal implant system is assembled it is then possible to correct anatomical deformities and stabilize the spine. In the ideal circumstance, the fixation elements are located in a colinear position substantially parallel to the vertebral column. However, in many circumstances particular vertebrae may deviate from this colinear position. Under these circumstances, it is often necessary to contour the rod in the saggital plane to account for abnormal lateral curvatures of the spine, such as scoloitic curvatures. After the rod has been contoured as dictated by the anatomy, the fixation hooks or bone screws can be engaged directly to the laterally offset vertebrae. This lateral offset of the vertebral column in the saggital plane can also be accommodated by a spinal fixation system of the type shown in the patent to Steffee U.S. Pat. No. 4,771,767, in which a number of smaller rods are engaged between lateral connectors. Other related systems provide means for laterally offsetting the screw from the spinal rod, such as systems shown in the patents to Steffee, U.S. Pat. No. 4,719,905; Howland, U.S. Pat. No. 4,653,481; and Frigg, U.S. Pat. No. 5,002,542.

One difficulty with spinal fixation systems of the prior art, and particularly those utilizing spinal rods, is that contouring the rod in the saggital plane can often be difficult, particularly since the rod must also be contoured to the normal cervical and lumbar curvatures of the spine. Three dimensional rod contouring is often physically difficult and is sometimes not possible in the space available for a particular patient.

To date, no spinal fixation system has been developed which adequately and simply addresses this problem by eliminating the need to contour the fixation rod in the saggital plane. The patent to Frigg '542 shows a pedicle screw clamp which is offset from the fixation rod and which includes means for varying the distance between the center of the rod and pedicle screw. In Frigg, a pair of splined surfaces is provided which are engaged by way of a special offset hook configuration. The Frigg device is not readily adapted to mount a variety of spinal fixation elements, such as bone screws or fixation hooks. Moreover, the Frigg pedicle screw clamp requires a specially configured hook to engage the spinal rod.

Consequently, there remains a need in the field of spinal fixation for a connector which acts as an intermediary component between the spinal rod and a vertebral fixation element, such as a bone screw or hook, to laterally offset the element from the spinal rod.

SUMMARY OF THE INVENTION

In recognition of this need in the field of spinal fixation, the present invention contemplates a lateral offset connector which permits engagement of a vertebral fixation element to a spinal rod, and particularly which accommodates variations in the lateral distance between the fixation element and the rod. In the preferred embodiment, the lateral offset connector includes a head portion from which a pair of parallel arms extend to form a slot opening between the arms. The arms are configured with a plurality of grooves on the underside of the arms which are aligned between the arms perpendicular to the longitudinal axis of the connector. The grooves are configured to receive the spinal rod therein.

The slot opening between the arms is configured to receive an eyebolt engagement assembly therebetween. The eyebolt is disposed between the arms of the connector with the spinal rod extending through the eyebolt bore. A nut is threaded onto the threaded post of the eyebolt to clamp the spinal rod between the eyebolt and the aligned grooves of the pair of connector arms.

The offset connector further includes a threaded post extending from the end of the connector for engagement with the vertebral fixation element, such as the bone screw or hook. A nut clamps the fixation element between a rounded shoulder of the connector and the nut.

One benefit of the present invention is realized by the plurality of grooves in the arms of the lateral offset connector. The grooves provide means for readily engaging the bone screw to a spinal rod where the lateral distance between these components is variable. The lateral offset connector of this invention, therefore, eliminates the need for contouring the rod in the saggital plane.

Another benefit of the lateral offset connector is that it is readily adapted to connect a variety of vertebral fixation elements, such as hooks and screws. No modification in the design of the fixation elements is required since the configuration of the offset of the present invention emulates the standard non-adjustable fixation of rod-type spinal implant systems.

The lateral offset connector realizes one object of the invention to provide a simple and efficient intermediary component between the spinal rod and the fixation element. The eyebolt connection of the offset connector to the spinal rod provides a simple engagement in two degrees of freedom, thereby simplifying assembly of the spinal fixation system within a patient.

Other benefits and objects of the present invention will become apparent from the following written description of the preferred embodiment, considered along with the accompanying figures.

DESCRIPTION OF THE PREFERRED EMBODIMENT

Figure 1:
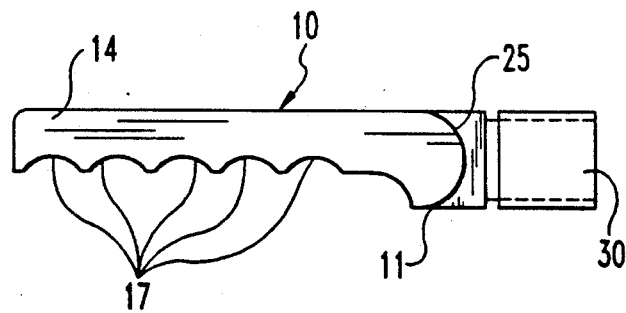
FIG. 1 is a side elevational view of the lateral offset connector of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
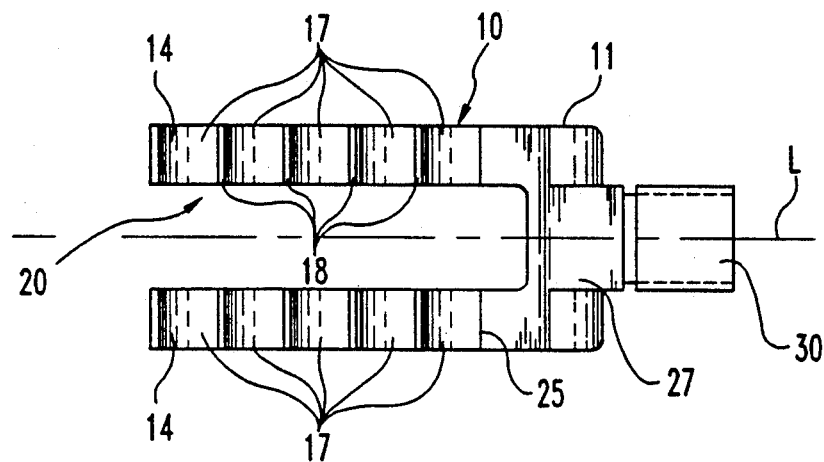
FIG. 2 is a bottom elevational view of the lateral offset connector shown in FIG. 1.

A lateral offset connector 10 according to the present invention is illustrated in FIGS. 1 and 2. The lateral offset connector 10 is preferably formed from medical grade stainless steel or other biocompatible material. The connector 10 includes a head 11 to which a pair of parallel arms 14 are integrally engaged. The arms are formed with a plurality of parallel grooves 17 with lands 18 interspersed between the grooves. The grooves 17 are aligned between each of the arms 14, perpendicular to the longitudinal axis L of the arm 14. Preferably, the grooves 17 are uniformly spaced relative to each other along the longitudinal axis L. The arms 14 are disposed apart from each other to define a slot opening 20 therebetween.

The head 11 of the lateral offset connector 10 includes a rounded shoulder 25. A guide portion 27 is formed along the longitudinal axis L of the offset connector and includes a threaded post 30 extending therefrom. In the preferred embodiment, the guide portion 27 is rectangular in cross-section and projects slightly out from the surface of the rounded shoulder 25, as shown more clearly in FIG. 2.

Figure 3:
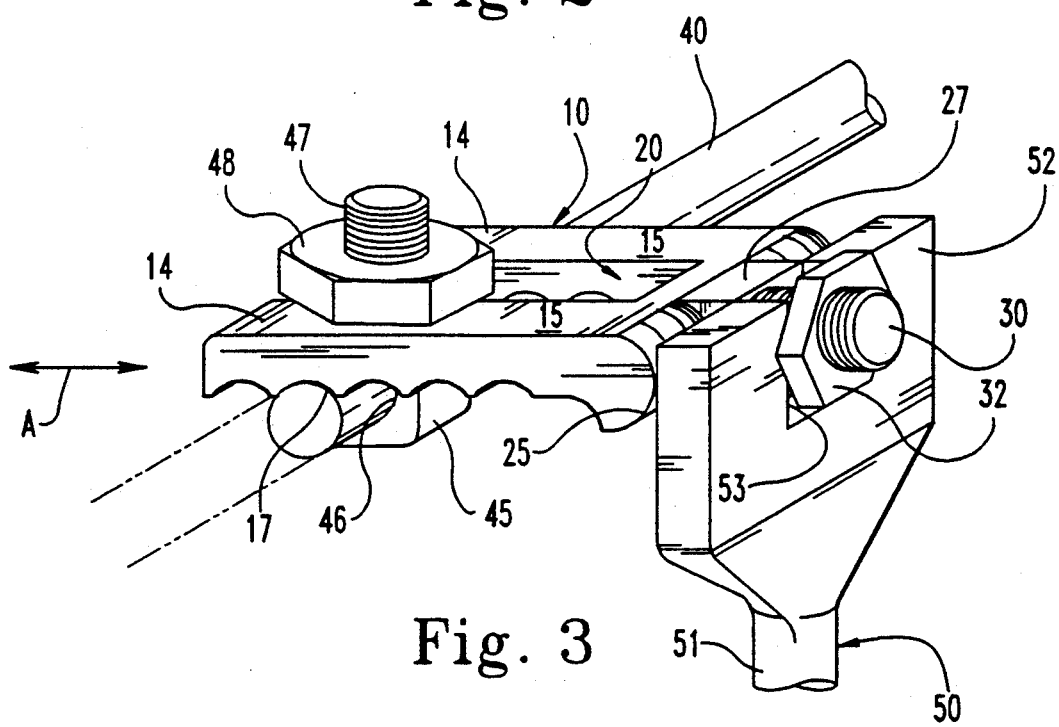
FIG. 3 is an isometric view of the lateral offset connector of the present invention shown engaged between a spinal fixation rod and a bone screw.

The lateral offset connector 10 is adapted to be engaged to a spinal rod 40, as depicted in FIG. 3. More particularly, the rod 40 is situated within a pair of grooves 17 aligned between the arms 14. In one specific embodiment, the grooves are formed at a radius of 0.094 inches (2.4 mm) to accommodate standard spinal rods of 0.188 inch (4.78 mm) or inch (6.35 mm) diameter. As appears in FIG. 1, the grooves are cut so to form an arc less than a complete semi-circle. Thus, even the larger spinal rod 0.250 inch diameter) can be accepted within the groove radius of the specific embodiment. The grooves must span enough of an arc to adequately retain the rod 40 within the groove 17 to restrain the offset connector 10 from lateral movement relative to the rod.

In an important feature of the invention, the slot opening 20 provides space for engagement of an eyebolt 45 between the arms 14. The eyebolt 45 defines a bore 46 through which the spinal rod 40 extends. The eyebolt 45 also includes a threaded post 47 extending from the eyebolt onto which a locknut 48 can be engaged. The eyebolt 45 can preferably be a ¼ inch eyebolt/locknut assembly provided by Danek Medical, Inc. as part number 808-029 for use with the Danek TSRH spinal implant system.

In the preferred use of the lateral offset connector 10, the eyebolt 45 is situated between the pair of parallel arms 14 with the spinal fixation rod 40 extending through the bore 46. With the arms 14 straddling the eyebolt 45 the rod 40 is situated within an aligned pair of grooves 17. The eyebolt 45 is situated within the slot opening 20 of the connector so that the threaded post 47 extends upward through the slot opening 20. The locknut 48 is then threaded onto the threaded post 47 until it contacts the upper face 15 of the pair of arms 14. As the locknut 48 is tightened onto the threaded post 47, it pushes the arms 14 downward so that the spinal rod 40 is clamped between the eyebolt bore 46 and the grooves 17 on the pair of arms 14, in the manner of a three-point shear clamp. In one specific embodiment, the slot opening 20 is 0.255 inches (6.48 mm) wide and 0.938 inches (23.83 mm) deep to accommodate a standard eyebolt, such as the Danek eyebolt No. 808-029.

Within the scope of the present invention means are provided on the lateral offset connector 10 for mating with a vertebral fixation element, such as a bone screw 50, as shown in FIG. 3. The bone screw 50 includes a threaded shaft 51 for engaging the pedicle of a vertebrae, for instance, and a head portion 52 which is configured to form a yoke 53. The bone screw 50 is connected to the offset connector 10 with the yoke 53 contacting the rounded shoulder 25 of the head portion 11. The guide portion 27 extends between the arms of the yoke 53 of the bone screw 50 to properly orient the bone screw 50. The rectangular configuration of the guide portion 27 engages the arms of the yoke 53 so that the bone screw 50 is restrained from twisting about the longitudinal axis L of the offset connector 10. Any such twisting moment is transmitted directly through the guide portion 27 and arms 14 of the offset connector 10 to be reacted by the spinal rod 40.

As with the eyebolt 45, a nut 32 is threaded onto the threaded post 30 extending from the offset connector 10 to firmly engage the head 52 of the bone screw 50 between the nut 32 and the rounded shoulder 25. The threaded post 30 is preferably dimensioned to emulate a standard eyebolt (such as the Danek 808-029 eyebolt), so that no modification of the design of the bone screw is required. The rounded shoulder 25 is provided so that the bone screw 50 can be engaged to the offset connector 10 at orientations other than perpendicular to the connector axis L, as may be required by the local geometry of the vertebral column. In one specific embodiment, the rounded shoulder 25 is formed at a radius of 0.250 inches (6.35 mm).

In one specific embodiment, the bone screw 50 can be a sacral spinal screw provided by Danek Medical as part number 808-225, or other similar screw. It is understood that while the bone screw 50 in the preferred embodiment is described as having an open yoke configuration for the head of the screw, a closed head bone screw can also be utilized provided that there is an opening through which the threaded post 30 can extend. It is, however, preferable to use an open yoke configured bone screw so that the bone screw 50 can be threaded into the vertebrae and the offset connector 10 subsequently fixed between the bone screw and the fixation rod 40.

In a typical circumstance, the spinal rod 40 and the bone screw 50 will already be in position relative to the vertebral column of the patient. It is therefore critical that the connection between the bone screw 50 and spinal rod 40 have some means to account for differences in the lateral distance between these two components. While prior devices required bending or contouring of the spinal rod 40 in the saggital plane so that it is close to the bone screw, the present invention provides a connector which can accommodate a wide range of lateral distances between the bone screw and the spinal rod. Specifically, the lateral offset connector connector 10 can be moved back and forth between the bone screw 50 and the fixation rod 40, as shown by the arrow A in FIG. 3, to adjust to the lateral distance between these two components. All that is required is that the rod 40 be engaged within an appropriate pair of grooves 17 when the offset connector 10 is engaged to the bone screw 50. In the illustrated embodiment, five such grooves 17 are provided at 0.162 inch (4.11 mm) intervals. It has been found that this arrangement of grooves accommodates most abnormal curvature conditions. Naturally, an offset connector can be provided with longer legs 14 having more grooves to account for greater lateral distances between the spinal rod 40 and the vertebral fixation element 50.

Use of the eyebolt 45 to clamp the offset connector 10 to the rod 40 also permits adjustment of the connector along the longitudinal length of the spinal rod. This feature is important when the offset connector 10 is first engaged to a bone screw 50 which is already threaded into a vertebra. With the eyebolt 45 freely sliding along the spinal rod 40, the position of the offset connector 10 can be oriented so that the guide portion 27 is aligned with the yoke 53 of the bone screw 50. The connector 10 can then be moved laterally until the guide portion 27 slides within the yoke 53. At this point, the two nuts 32 and 48 can be tightened to rigidly connect the bone screw 50 to the spinal rod 40.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. While the preferred embodiment of the lateral offset connector 10 is configured for connecting a bone screw 50 to the spinal rod 40, other vertebral fixation elements are contemplated. For instance, a pedicle hook can also be engaged to the threaded post 30 of the connector, such as the Danek pedicle halftop hook, provided as part number 808-005 or the Danek large laminar halftop hook part number 808-008.

Similarly, while dimensions of a specific embodiment of the offset connector 10 have been disclosed herein, these dimensions are not intended to be restrictive in nature. In other words, for a given anatomy changes in dimensions of specific portions of the connector 10 can be readily made without departing from the spirit of the invention.

What is claimed is:

1. A lateral offset connector for use in a spinal implant system to connect a vertebral fixation element to a spinal rod extending adjacent the vertebral column in a patient, the connector comprising:
    a head portion;
    a pair of parallel arms integrally extending from said head portion along a longitudinal axis, said pair of arms being displaced from each other perpendicular to said longitudinal axis to define a slot opening therebetween, said slot opening being sized to receive an eyebolt assembly therethrough;
    a plurality of grooves defined in a surface of each of said pair of arms, each of said plurality of grooves being aligned between said pair of arms and each of said plurality of grooves being formed at a radius configured to receive the spinal rod therein;
    a threaded post integrally extending from said head portion along said longitudinal axis in a direction opposite said pair of parallel arms; and
    a nut for engaging said threaded post, whereby the vertebral fixation element is clamped between said head portion and said nut when said nut is engaged on said threaded post.

2. The lateral offset connector of claim 1, wherein said head portion includes a curved shoulder arranged to contact the vertebral fixation element when the fixation element is clamped between said head portion and said nut.

3. A lateral offset connector for use in a spinal implant system to connect an open yoke vertebral fixation element to a spinal rod extending adjacent the vertebral column in a patient, the connector comprising:
    a head portion;
    a pair of parallel arms integrally extending from said head portion along a longitudinal axis, said pair of arms being displaced from each other perpendicular to said longitudinal axis to define a slot opening therebetween, said slot opening being sized to receive an eyebolt assembly therethrough;
    a plurality of grooves defined in a surface of each of said pair of arms, each of said plurality of grooves being aligned between said pair of arms and each of said plurality of grooves being formed at a radius configured to receive the spinal rod therein;
    a threaded post integrally extending from said head portion along said longitudinal axis in a direction opposite said pair of parallel arms; and
    a nut for engaging said threaded post, whereby the vertebral fixation element is clamped between said head portion and said nut when said nut is engaged on said threaded post,
    wherein said head portion includes a guide portion with said threaded post extending from said guide portion, said guide portion having a rectangular cross-section along said longitudinal axis to engage within the open yoke of the vertebral fixation element to restrain rotation of the fixation element about said longitudinal axis.

4. An assembly for use in a spinal implant system to connect a plurality of vertebral fixation element to a spinal rod extending adjacent the vertebral column in a patient in which the plurality of fixation elements are non-colinear, the assembly comprising:
    a lateral offset connector including;
        a head portion;
        a pair of parallel arms integrally extending from said head portion along a longitudinal axis, said pair of arms being displaced from each other perpendicular to said longitudinal axis to define a slot opening therebetween;

a plurality of grooves defined in a surface of each of said pair of arms, each of said plurality of grooves being aligned between said pair of arms and each of said plurality of grooves being formed at a radius configured to receive the spinal rod therein perpendicular to said longitudinal axis;

a threaded post integrally extending from said head portion along said longitudinal axis in a direction opposite said pair of parallel arms; and a nut for engaging said threaded post, whereby the vertebral fixation element is clamped between said head portion and said nut when said nut is engaged on said threaded post;

means, disposed within said slot opening, for clamping said pair of arms to the spinal rod with the spinal rod disposed within one of said plurality of grooves in each of said pair of arms, whereby the spinal rod can be adjustably disposed within said one of said plurality of grooves with said pair of arms spanning the distance between the spinal rod and the vertebral fixation element.

* * * * *